United States Patent
Yeon

(10) Patent No.: US 11,276,833 B2
(45) Date of Patent: Mar. 15, 2022

(54) METHOD FOR MANUFACTURING QUANTUM DOT LAYER, METHOD FOR MANUFACTURING LUMINESCENCE DEVICE INCLUDING THE QUANTUM DOT LAYER, AND DISPLAY DEVICE INCLUDING THE QUANTUM DOT LAYER

(71) Applicant: Samsung Display Co., Ltd., Yongin-si (KR)

(72) Inventor: Sungmo Yeon, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 16/784,006

(22) Filed: Feb. 6, 2020

(65) Prior Publication Data
US 2020/0313105 A1    Oct. 1, 2020

(30) Foreign Application Priority Data

Mar. 25, 2019   (KR) .......................... 10-2019-0033616

(51) Int. Cl.
*H01L 51/50*    (2006.01)
*H01L 51/56*    (2006.01)
(Continued)

(52) U.S. Cl.
CPC ............ *H01L 51/502* (2013.01); *B82Y 40/00* (2013.01); *C04B 40/029* (2013.01); *C04B 41/4535* (2013.01); *C07C 211/06* (2013.01); *C08G 18/3876* (2013.01); *C08G 18/834* (2013.01); *C08G 65/332* (2013.01);
(Continued)

(58) Field of Classification Search
CPC ... C04B 40/029; C04B 41/4535; B82Y 40/00; G01N 27/4145; C07C 211/06; C09B 29/0807; C09B 68/446; C08G 18/834; C08G 65/332; H01L 51/502; H01L 51/5012; H01L 21/31058; H01L 51/56;
(Continued)

(56) References Cited

U.S. PATENT DOCUMENTS 5,650,854 A    7/1997 Sugawara
9,666,821 B2   5/2017 Park et al.
(Continued)

FOREIGN PATENT DOCUMENTS

KR    10-2010-0093858    8/2010
KR    10-1724032         4/2017

OTHER PUBLICATIONS

Park et al., Programmable DNA Self-Assemblies for Nanoscale Organization of Ligands and Proteins, Nano Letters, Mar. 8, 2005, pp. 729-733, vol. 5, No. 4, American Chemical Society.

*Primary Examiner* — Galina G Yushina
(74) *Attorney, Agent, or Firm* — H.C. Park & Associates, PLC

(57) ABSTRACT

A method for manufacturing a quantum dots layer including providing a substrate on which a first electrode, a second electrode, and a third electrode are disposed; providing a first mixed solution including a first quantum dots, which have been surface-treated to have a first polarity, on the first to third electrodes; providing a second polarity opposite to the first polarity to the first electrode resulting in deposition of the first quantum dots on the first electrode; and drying the first mixed solution to form a first quantum dots layer.

13 Claims, 17 Drawing Sheets

(51) Int. Cl.
<table>
<tr><td>C09B 3/48</td><td>(2006.01)</td></tr>
<tr><td>C07C 211/06</td><td>(2006.01)</td></tr>
<tr><td>C08L 101/10</td><td>(2006.01)</td></tr>
<tr><td>C08G 18/83</td><td>(2006.01)</td></tr>
<tr><td>C08G 65/332</td><td>(2006.01)</td></tr>
<tr><td>H01L 21/3105</td><td>(2006.01)</td></tr>
<tr><td>C09B 29/08</td><td>(2006.01)</td></tr>
<tr><td>C04B 40/02</td><td>(2006.01)</td></tr>
<tr><td>C04B 41/45</td><td>(2006.01)</td></tr>
<tr><td>C08G 18/38</td><td>(2006.01)</td></tr>
<tr><td>H01L 51/00</td><td>(2006.01)</td></tr>
<tr><td>G09G 3/30</td><td>(2006.01)</td></tr>
<tr><td>C09B 67/00</td><td>(2006.01)</td></tr>
<tr><td>B82Y 40/00</td><td>(2011.01)</td></tr>
</table>

(52) U.S. Cl.
CPC .............. *C08L 101/10* (2013.01); *C09B 3/48* (2013.01); *C09B 29/0807* (2013.01); *C09B 68/446* (2013.01); *G09G 3/30* (2013.01); *H01L 21/31058* (2013.01); *H01L 51/0014* (2013.01); *H01L 51/5012* (2013.01); *H01L 51/56* (2013.01)

(58) Field of Classification Search
CPC . H01L 51/014; H01L 21/0012; H01L 27/3211
See application file for complete search history.

(56) References Cited

U.S. PATENT DOCUMENTS

| | | | | |
|---|---|---|---|---|
| 2012/0132888 A1* | 5/2012 | Kwak | .................... | B82Y 20/00 257/13 |
| 2013/0056705 A1* | 3/2013 | Kim | ...................... | B82Y 40/00 257/13 |
| 2015/0380249 A1* | 12/2015 | Gouk | ................ | H01L 29/66803 438/559 |
| 2016/0218141 A1* | 7/2016 | Cai | ......................... | H01L 33/08 |
| 2019/0081263 A1* | 3/2019 | Park | ........................ | H01L 33/06 |
| 2019/0189711 A1* | 6/2019 | Ryoo | .................. | H01L 51/5221 |
| 2019/0214594 A1* | 7/2019 | Jang | .................... | H01L 51/0003 |
| 2019/0388883 A1* | 12/2019 | Tan | ...................... | C25B 11/051 |
| 2020/0023084 A1* | 1/2020 | Bawendi | ............. | A61K 49/1839 |
| 2020/0194522 A1* | 6/2020 | Lee | .................... | H01L 51/0007 |
| 2020/0259110 A1* | 8/2020 | Angioni | .............. | H01L 51/5056 |
| 2021/0078867 A1* | 3/2021 | Lux | .................... | A61K 49/1881 |

* cited by examiner

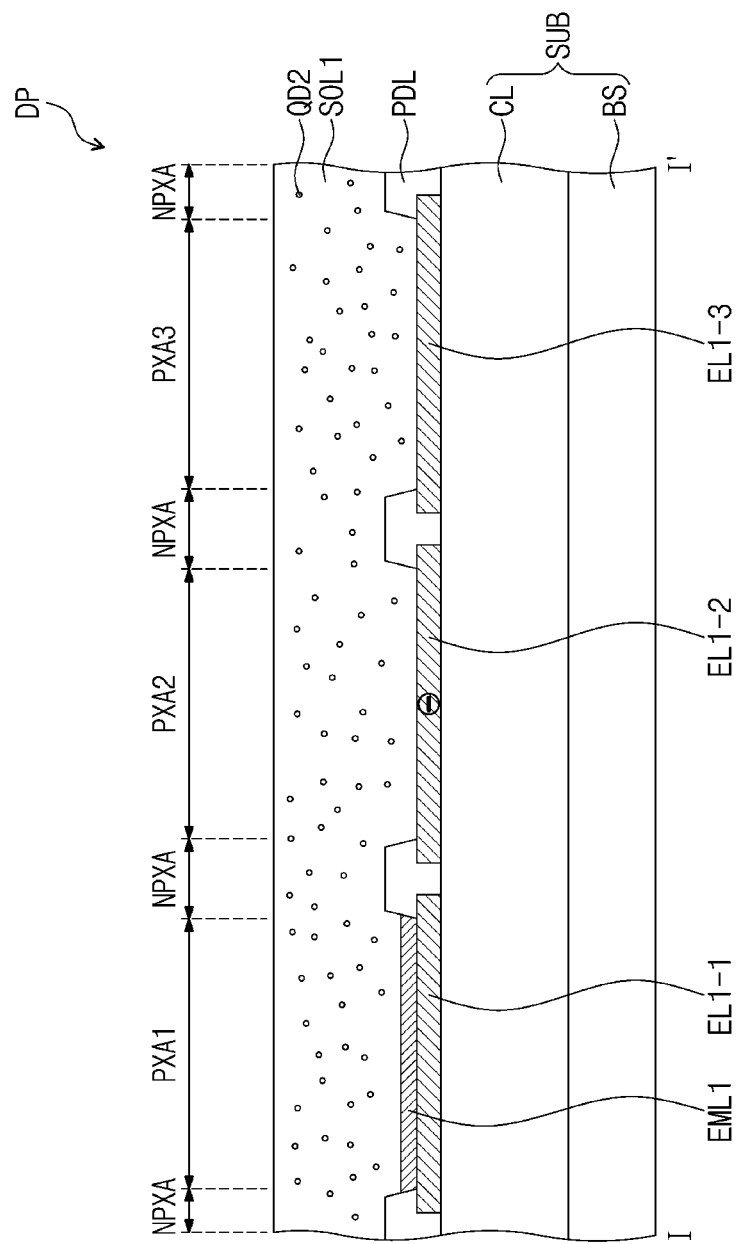

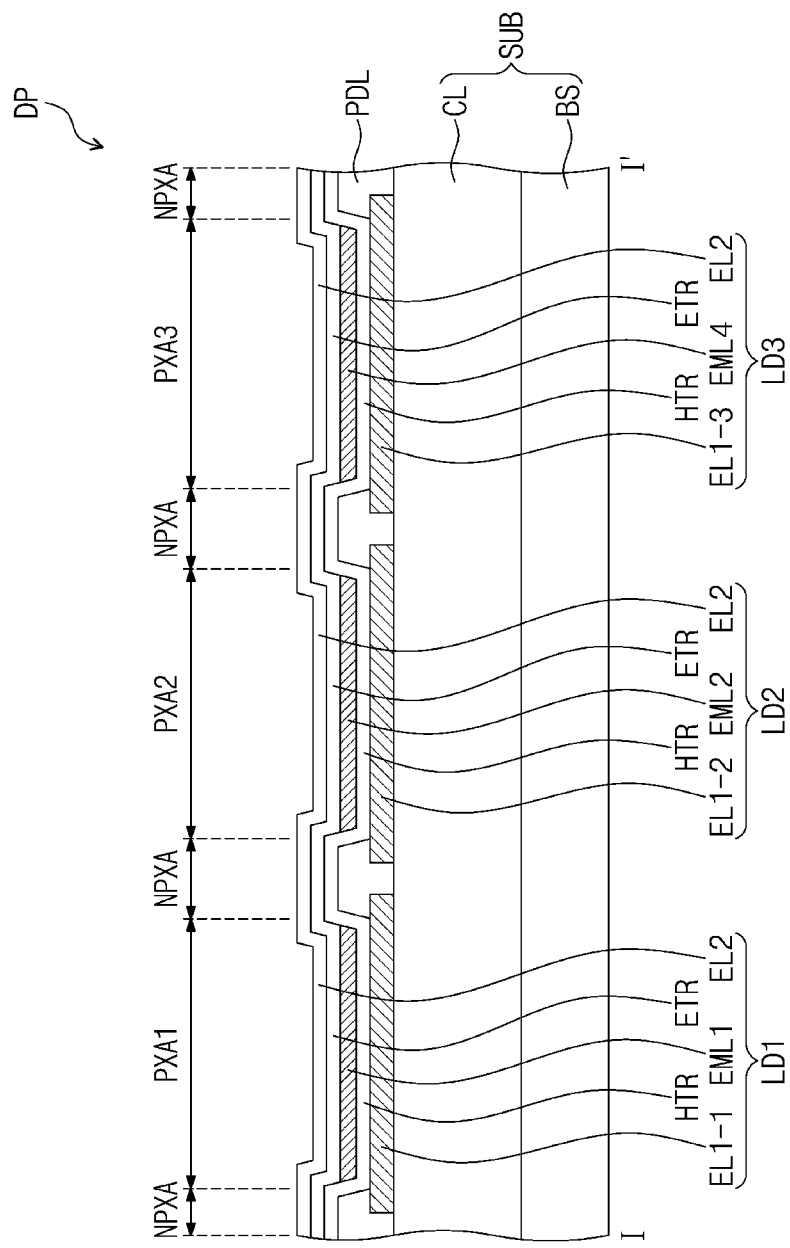

METHOD FOR MANUFACTURING QUANTUM DOT LAYER, METHOD FOR MANUFACTURING LUMINESCENCE DEVICE INCLUDING THE QUANTUM DOT LAYER, AND DISPLAY DEVICE INCLUDING THE QUANTUM DOT LAYER

CROSS-REFERENCE TO RELATED APPLICATION

This application claims priority from and the benefit of Korean Patent Application No. 10-2019-0033616, filed on Mar. 25, 2019, which is hereby incorporated by reference for all purposes as if fully set forth herein.

BACKGROUND

Field

Exemplary embodiments of the invention relate to a method for manufacturing a quantum dots layer, a method for manufacturing a luminescence device including the quantum dots layer, and a display device including the quantum dots layer.

Discussion of the Background

Electronic devices, such as a mobile communication terminal, a digital camera, a laptop computer, a monitor, and a television include a display device for displaying images.

In a display device, a quantum dot is actively used as a material for a luminescence device or for a light control layer. Typically, when manufacturing a luminescence device or light control layer which includes a quantum dots layer, quantum dots are deposited by using a fine metal mask. However, when quantum dots are deposited by using a fine metal mask, the mask may be warped as the mask area is widened, thereby making it more difficult to manufacture a large display device, while wasting material to increase process cost.

SUMMARY

Exemplary embodiments of the invention provide a method for manufacturing a quantum dots layer and a luminescence device including the quantum dots layer without a mask.

Exemplary embodiments of the invention also provide a display device including a quantum dots layer which is manufactured without using a mask.

Additional features of the invention will be set forth in the description which follows, and in part will be apparent from the description, or may be learned by practice of the invention.

An exemplary embodiment of the invention provides a method for manufacturing a quantum dots layer including: providing a substrate on which a first electrode, a second electrode, and a third electrode, which are spaced apart from each other on a plane, are disposed; providing a first mixed solution including a first quantum dots which has been surface-treated to have a first polarity on the first to third electrodes; providing a second polarity opposite to the first polarity to the first electrode; disposing the first quantum dots on the first electrode on which the second polarity is provided; and drying the first mixed solution to form a first quantum dots layer.

The providing of the first mixed solution on the first to third electrodes may include mixing a first base quantum dot with a base solution, which contains a polar material to prepare a first mixed solution.

The method may further include: providing a second mixed solution including a second quantum dots, which has been surface-treated to have the first polarity on the first to third electrodes; providing the second polarity to the second electrode; disposing the second quantum dots on the second electrode, which is provided with the second polarity; drying the second mixed solution to form a second quantum dots layer; providing a third mixed solution including a third quantum dots, which has been surface-treated to have the first polarity on the first to third electrodes; providing the second polarity to the third electrode; disposing the third quantum dots on the third electrode, which is provided with the second polarity; and drying the third mixed solution to form a third quantum dots layer.

The method may further include disposing a second electrode on the first to third quantum dots layers. The first quantum dots layer may emit red light, the second quantum dots layer may emit green light, and the third quantum dots layer may emit blue light.

The first polarity may be a positive polarity. The polar material may be an organic compound having an amino group and a silane group.

The polar material may be at least one among 3-aminopropyltriethoxysilane (APTES), 3-aminopropyltrimethoxysilane (APTMS), N-(6-aminohexyl)-3-aminopropyltrimethoxysilane (AHAPS), N-(2-aminoethyl)-3-aminopropylmethyldimethoxysilane (AEAPS), 3-aminopropyldimethylethoxysilane (APMES), and 3-(N, N-dimethyl)-aminopropyltrimethoxysilane (DMAPS).

The first polarity may be a negative polarity. The polar material may be an organic compound having a thiol group and a carboxyl group.

The polar material may be at least one selected from among mercaptoacetic acid derivatives, mercaptopropionic acid derivatives, mercaptobutyric acid derivatives, and mercaptovaleric acid derivatives.

The first quantum dots layer may be a quantum dots layer, which absorbs blue light and emits red light or green light.

The substrate may have an optical transmittance of 90% or more.

The disposing of the first quantum dots may further include providing the first polarity to the second electrode and the third electrode.

Another exemplary embodiment of the invention provides a method for manufacturing a luminescence device including: providing a substrate on which a first electrode is disposed; providing a first mixed solution including a quantum dot which has been surface-treated with a polar material to have a first polarity on the first electrode; providing a second polarity opposite to the first polarity to the first electrode; disposing the quantum dot on the first electrode on which the second polarity is provided; drying the first mixed solution to form a quantum dots layer; and disposing a second electrode on the quantum dots layer.

The polar material may be an organic compound having an amino group and a silane group, or a thiol group and a carboxyl group.

The polar material may be at least one selected from among 3-aminopropyltriethoxysilane (APTES), 3-aminopropyltrimethoxysilane (APTMS), N-(6-aminohexyl)-3-aminopropyltrimethoxysilane (AHAPS), N-(2-aminoethyl)-3-aminopropylmethyldimethoxysilane (AEAPS), 3-aminopropyldimethylethoxysilane (APMES), and 3-(N, N-dimethyl)-aminopropyltrimethoxysilane (DMAPS). Alternatively, the polar material may be at least one selected from among mercaptoacetic acid derivatives, mercaptopropionic acid derivatives, mercaptobutyric acid derivatives, and mercaptovaleric acid derivatives.

Another exemplary embodiment of the invention provides a display device including a first pixel area, a second pixel area, a third pixel area, a first luminescence device, a second luminescence device, and a third luminescence device. The first luminescence device, the second luminescence device, and the third luminescence device may have a one-to-one correspondence with the first pixel area, the second pixel area, and the third pixel area, respectively. Each of the first to third luminescence devices may include a first electrode, a second electrode, and a quantum dots layer. The quantum dots layer may include a quantum dot which is disposed between the first electrode and the second electrode, and has been surface-treated with a polar material. The polar material may be an organic compound having an amino group and a silane group, or a thiol group and a carboxyl group.

The polar material may be at least one selected from among 3-aminopropyltriethoxysilane (APTES), 3-aminopropyltrimethoxysilane (APTMS), N-(6-aminohexyl)-3-aminopropyltrimethoxysilane (AHAPS), N-(2-aminoethyl)-3-aminopropylmethyldimethoxysilane (AEAPS), 3-aminopropyldimethylethoxysilane (APMES), and 3-(N, N-dimethyl)-aminopropyltrimethoxysilane (DMAPS). Alternatively, the polar material may be at least one selected from among mercaptoacetic acid derivatives, mercaptopropionic acid derivatives, mercaptobutyric acid derivatives, and mercaptovaleric acid derivatives.

Each of the first to third luminescence devices may further include an electron transporting region and a hole transporting region. The electron transporting region may be disposed between the first electrode and the quantum dots layer. The hole transporting region may further include a hole transporting region disposed between the quantum dots layer and the second electrode.

The first luminescence device may emit red light, the second luminescence device may emit green light, and the third luminescence device may emit blue light.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the inventive concepts, and are incorporated in and constitute a part of this specification. The drawings illustrate exemplary embodiments of the inventive concept and, together with the description, serve to explain principles of the inventive concepts.

FIG. 5G is a cross-sectional view illustrating a step for providing a second mixed solution on first to third electrodes.

FIG. 6 is a cross-sectional view illustrating a display device on which a luminescence device formed by a method for manufacturing a luminescence device according to an exemplary embodiment is disposed.

DETAILED DESCRIPTION

Figure 1:
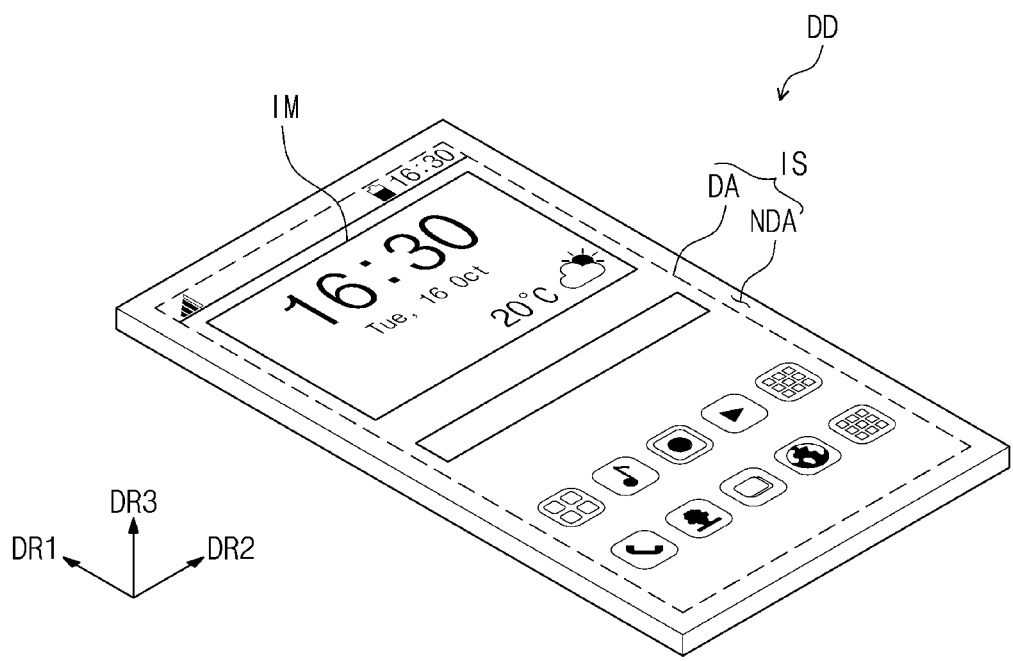
FIG. 1 is a perspective view of a display device according to an exemplary embodiment of the invention.

In the following description, for the purposes of explanation, numerous specific details are set forth in order to provide a thorough understanding of various exemplary embodiments of the invention. As used herein "embodiments" are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments of the invention will be described with reference to drawings.

FIG. 1 is a perspective view of a display device DD according to an exemplary embodiment of the invention. As illustrated in FIG. 1, the display device DD may display an image IM through a display surface IS. The display surface IS is parallel to a plane defined by a first direction axis DR1 and a second direction axis DR2. A third direction axis DR3 indicates a normal direction of the display surface IS, i.e., a thickness direction of the display device DD.

A front surface (or a top surface) and a back surface (or a bottom surface) of each member or unit which will be described below are defined according to the third direction axis DR3. However, the first to third direction axes DR1, DR2 and DR3 illustrated in FIG. 1 are merely exemplary directions, and the directions indicated by the first to third direction axes DR1, DR2 and DR3 are relative concepts, so that the directions may change into other directions. Hereinafter, the first to third directions refer to the same reference numerals as the directions indicated by the first to third direction axes DR1, DR2, and DR3, respectively.

In an exemplary embodiment of the invention, the display device DD having a planar display surface is illustrated, but the inventive concepts are not limited thereto. The display device DD may include a curved display surface or a stereoscopic display surface. The stereoscopic display surface may include a plurality of display areas indicating different directions from each other, and may also include, for example, a polygonal columnar display surface.

The display device DD may be a rigid display device. However, the inventive concepts are not limited thereto, and the display device DD may instead be a flexible display device DD. In this exemplary embodiment, the display device DD applicable to a portable terminal is exemplarily illustrated. Although not illustrated herein, electronic modules, a camera module, a power module, etc. mounted on a main board are accommodated in a housing (not illustrated) to constitute the portable terminal. The display device DD according to the inventive concepts may be applied to not only a large-sized electronic device such as a television, a monitor, but also a small- or medium-sized electronic device such as a tablet, a car navigation system, a game machine, a smart watch.

As illustrated FIG. 1, the display surface IS may include a display area DA, in which the image IM is displayed, and a non-display area NDA adjacent to the display area DA. The non-display area NDA is an area in which the image is not displayed. As an example of the image IM, icon images are illustrated in FIG. 1.

As illustrated in FIG. 1, the display area DA may have a rectangular shape. The non-display area NDA may surround the display area DA. However, the inventive concepts are not limited thereto, and the shape of the display area DA and the shape of the non-display area NDA may be relatively designed.

Figure 5A:
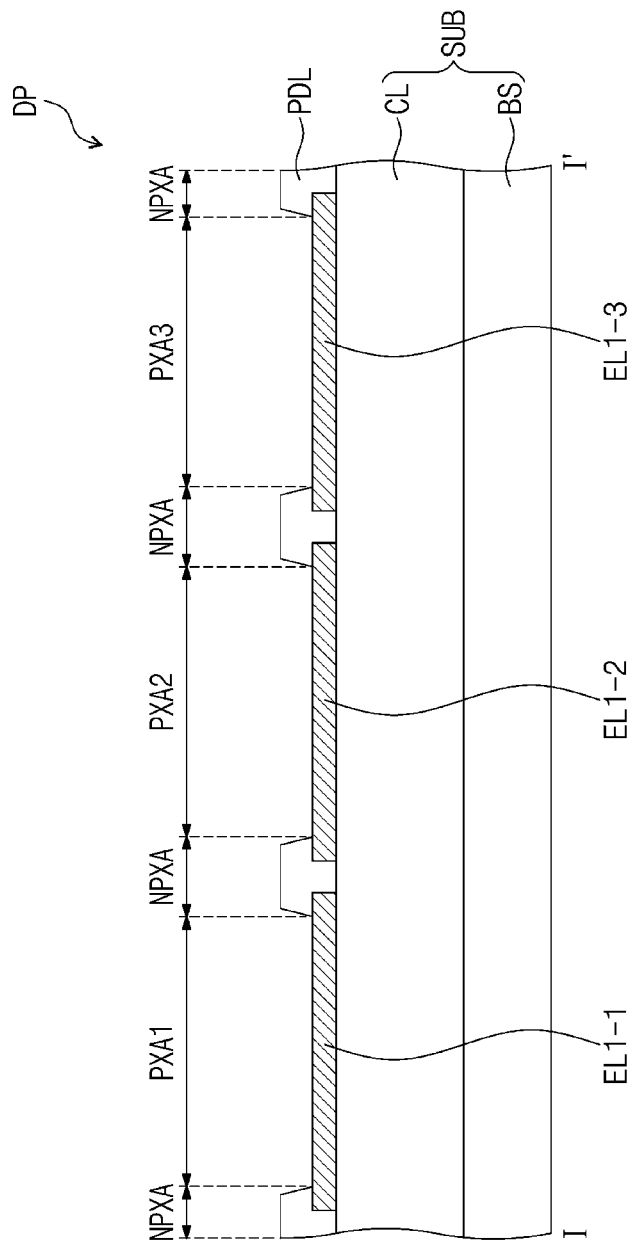
FIG. 5A is a cross-sectional view illustrating a step for providing a substrate on which first to third electrodes are formed.
Figure 5B:
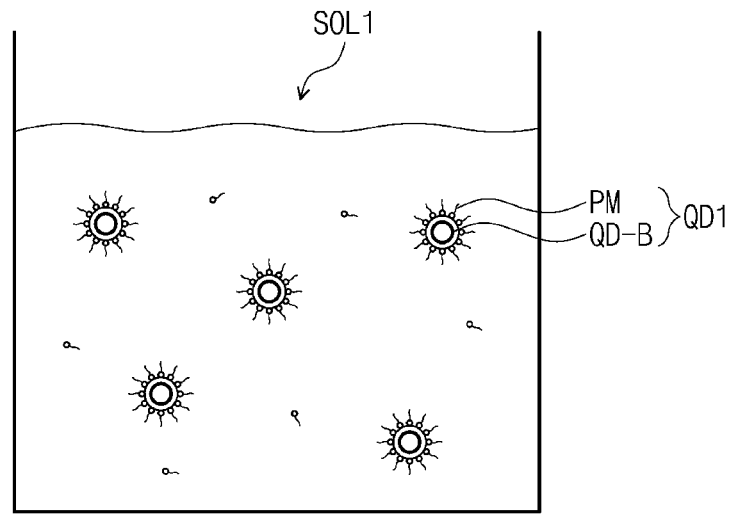
FIG. 5B is a view illustrating a step for preparing a first mixed solution.
Figure 5C:
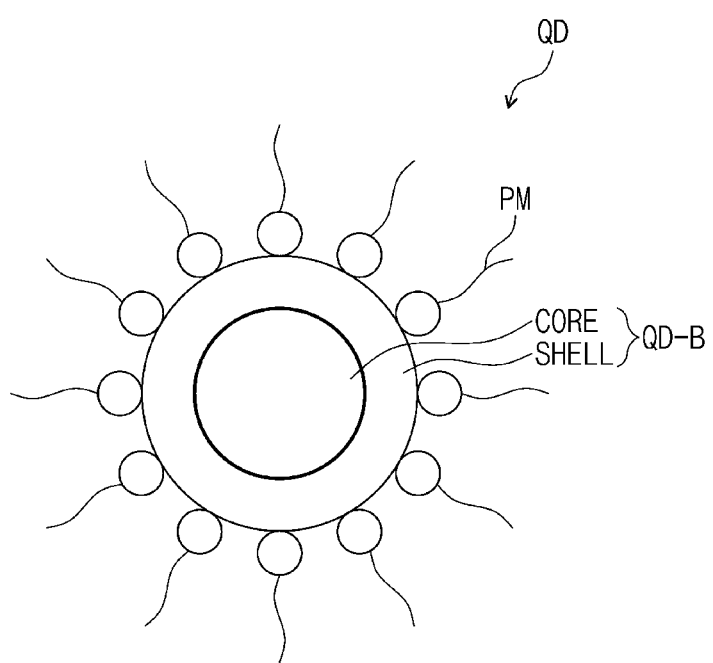
FIG. 5C is a perspective view illustrating a quantum dot luminous body which has been surface-treated with a polar material according to an exemplary embodiment.
Figure 5D:
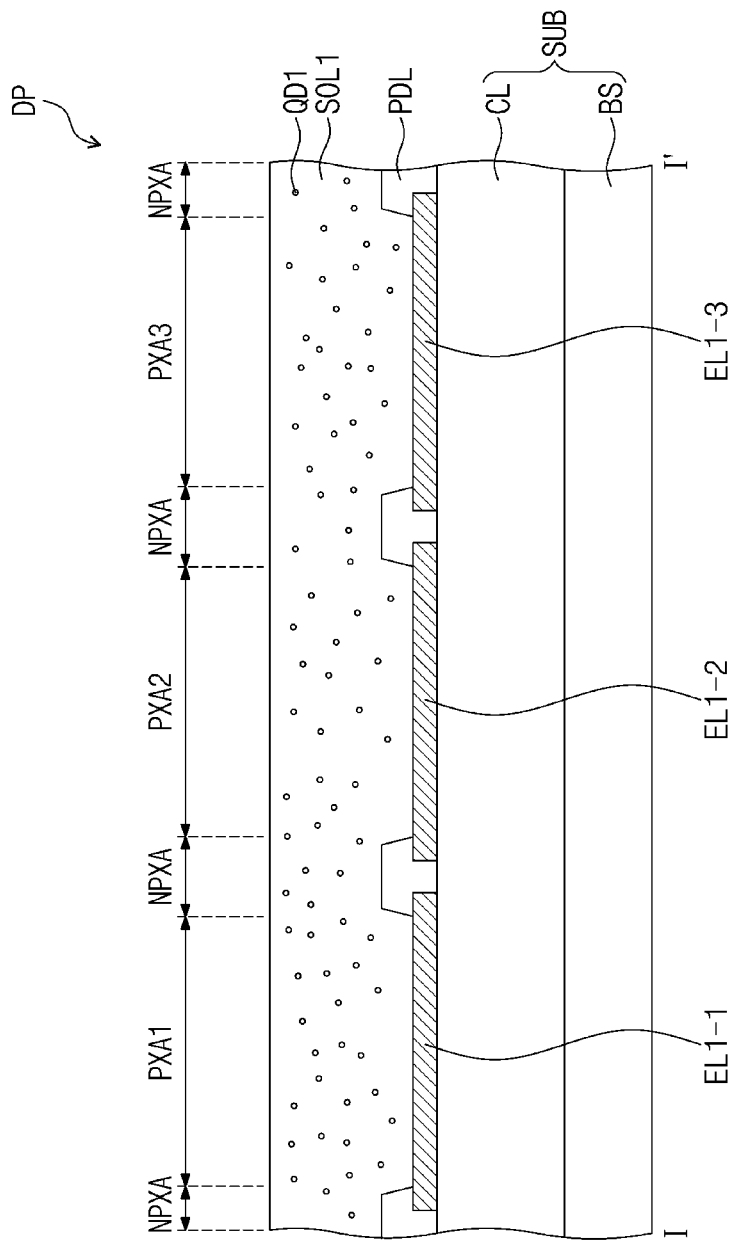
FIG. 5D is a cross-sectional view illustrating a step for providing a first mixed solution on first to third electrodes.
Figure 5E:
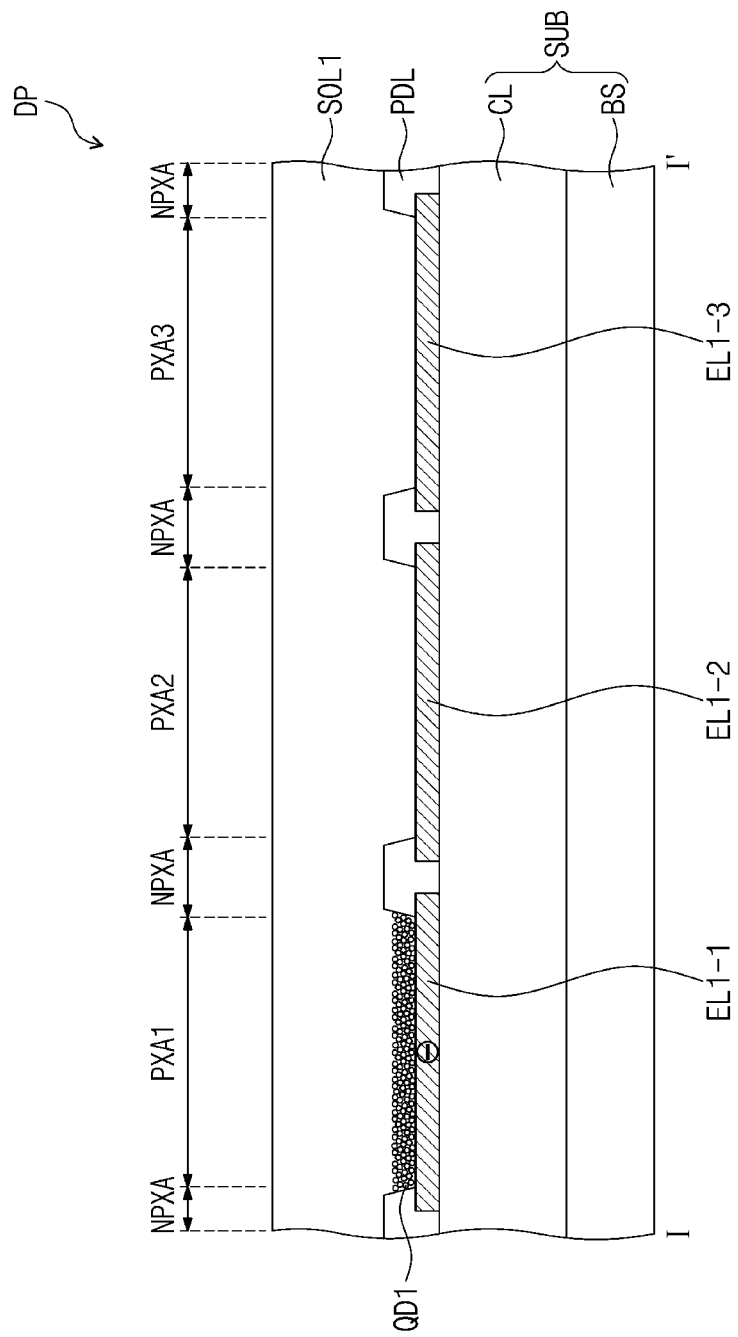
FIG. 5E is a cross-sectional view illustrating a step for providing a second polarity to a first electrode.
Figure 5F:
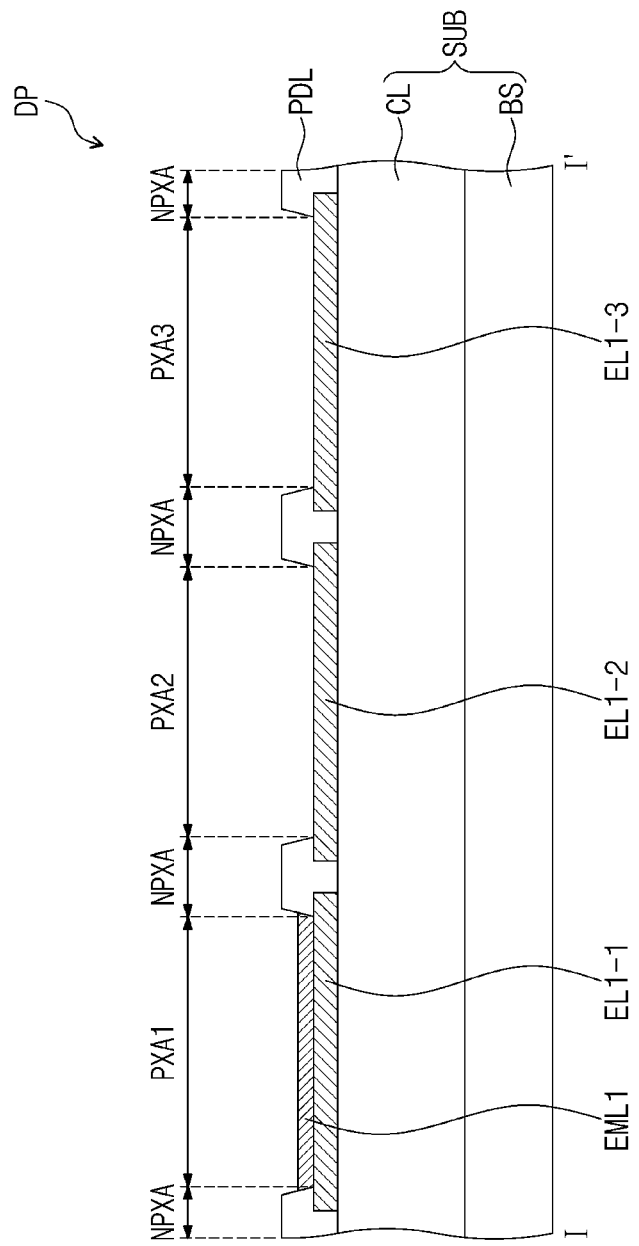
FIG. 5F is a cross-sectional view illustrating a step for drying a first mixed solution to form a first quantum dots layer.
Figure 5H:
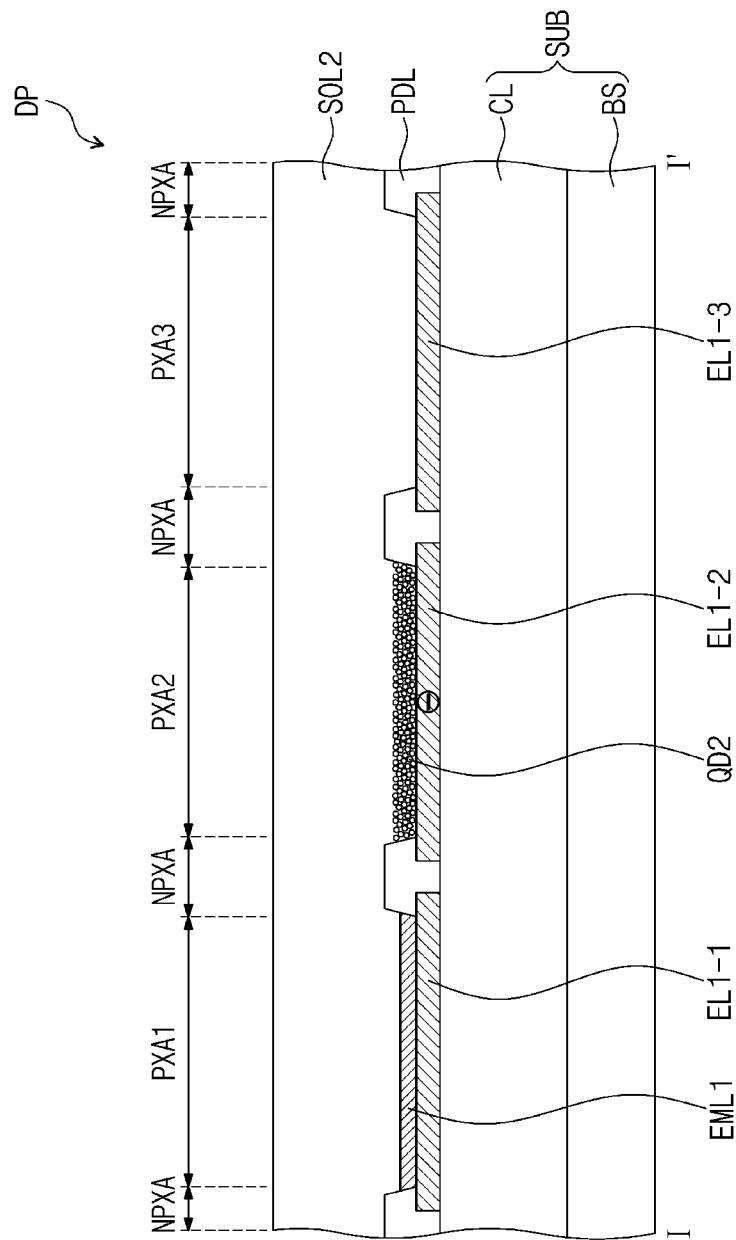
FIG. 5H is a cross-sectional view illustrating a step for providing a second polarity to a second electrode.
Figure 5I:
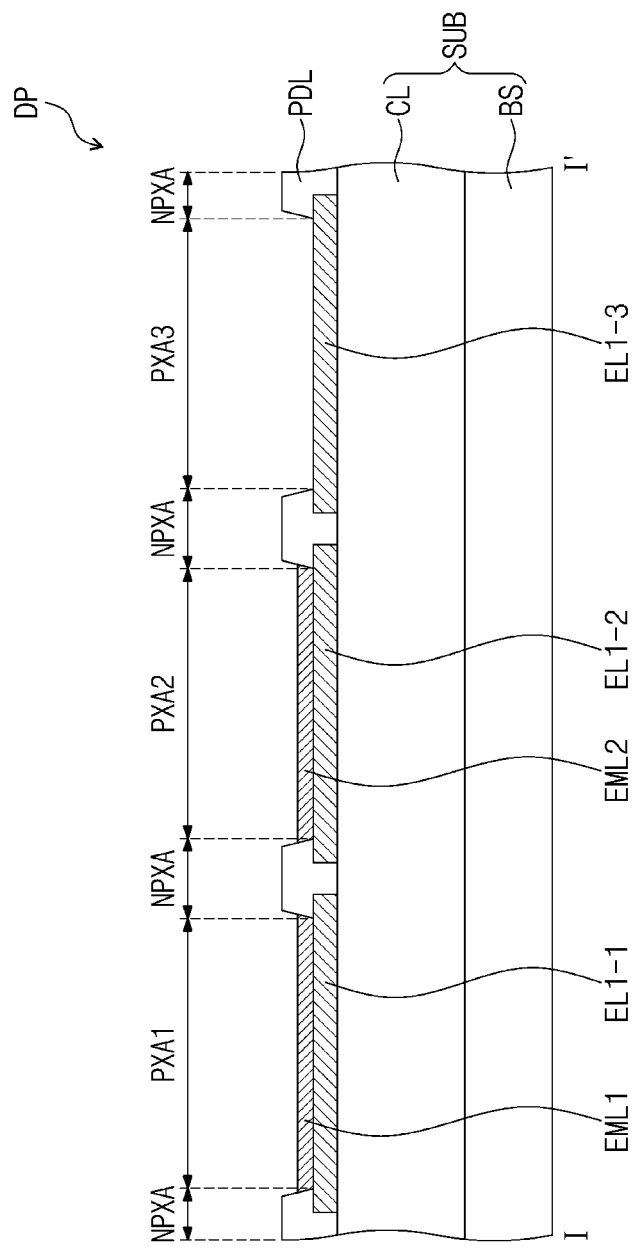
FIG. 5I is a cross-sectional view illustrating a step for drying a second mixed solution to form a second quantum dots layer.
Figure 5J:
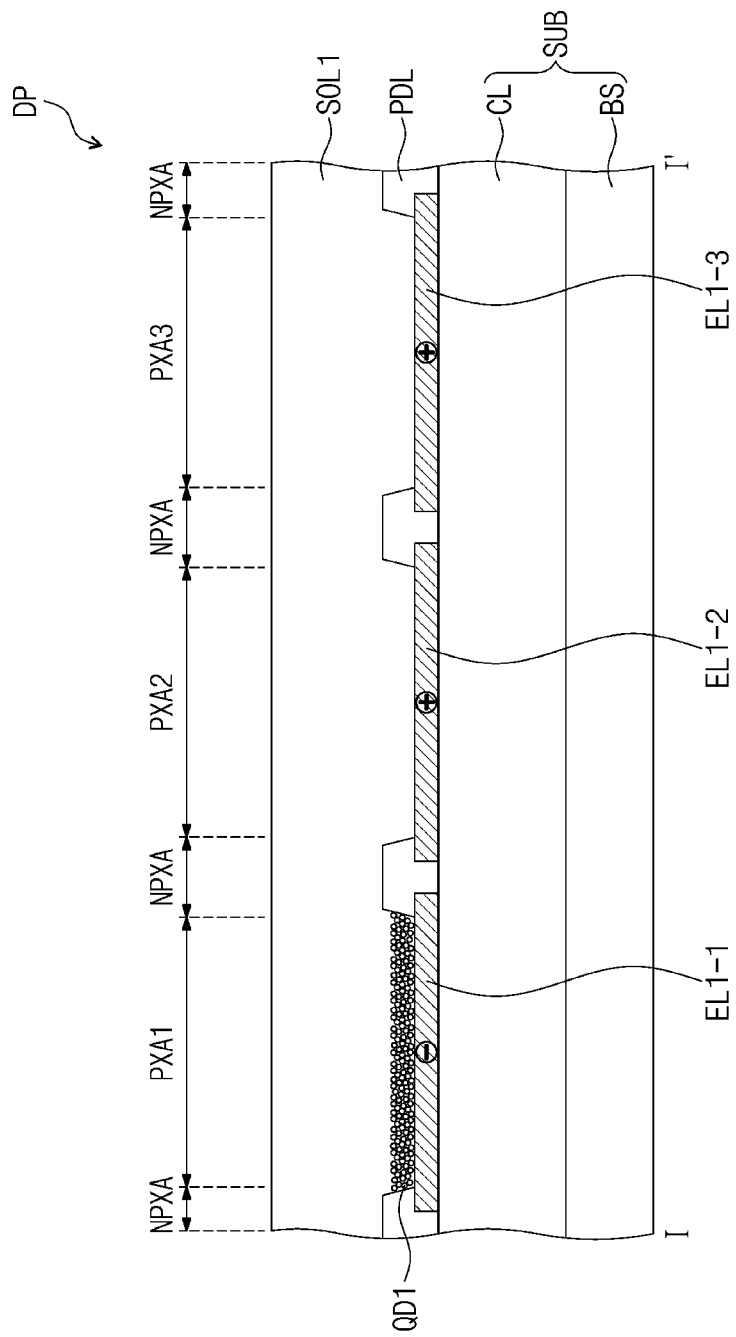
FIG. 5J is a cross-sectional view illustrating a step for providing a first polarity to a second electrode and a third electrode according to exemplary embodiment.
Figure 5K:
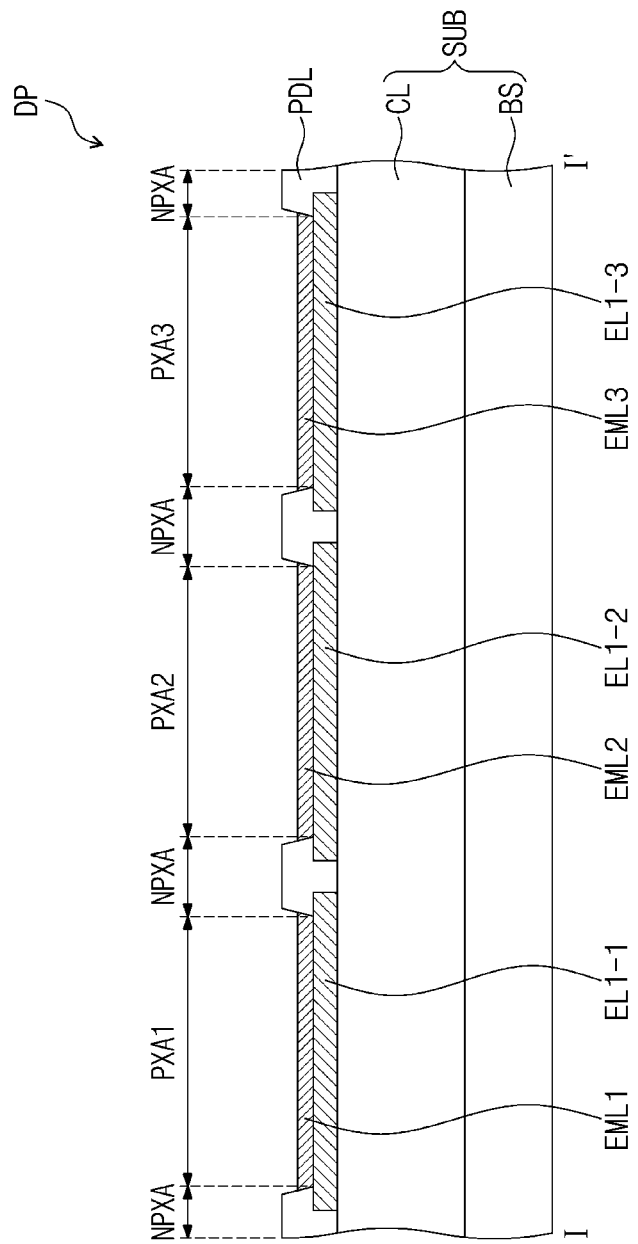
FIG. 5K is a cross-sectional view illustrating a substrate on which a quantum dots layer formed by a method for manufacturing a quantum dots layer according to an exemplary embodiment is disposed.
Figure 5L:
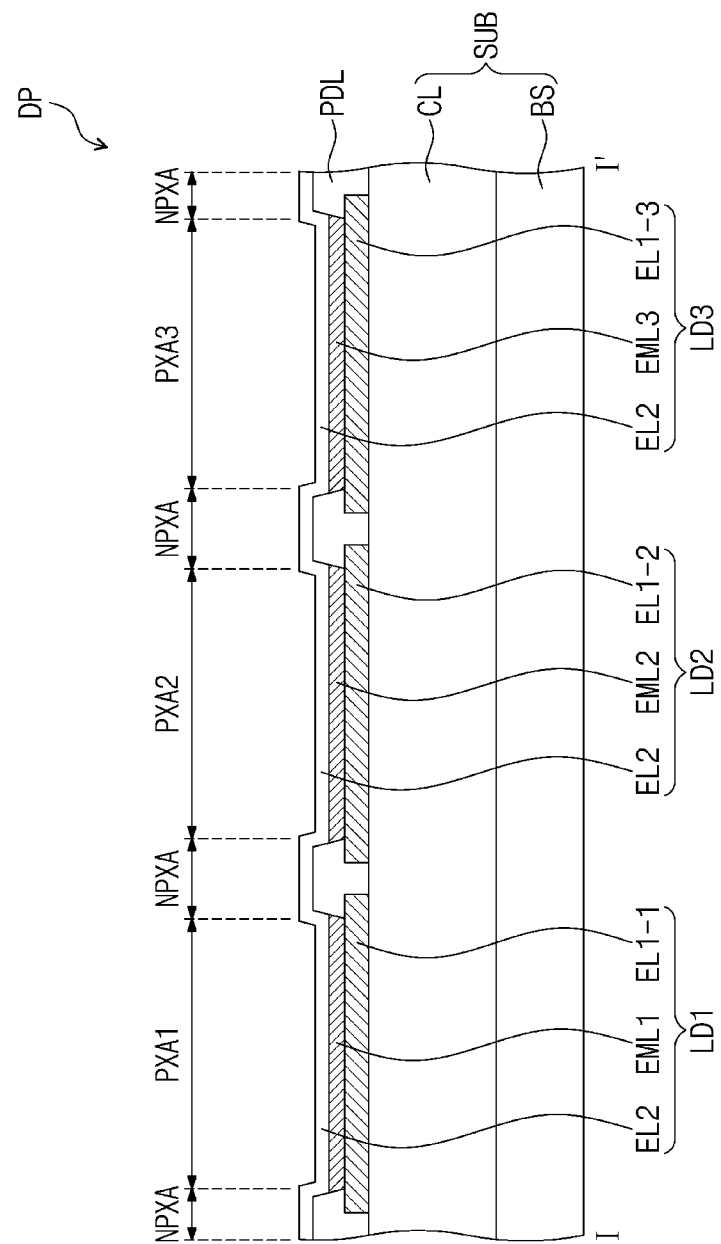
FIG. 5L is a cross-sectional view illustrating a display device on which a luminescence device formed by a method for manufacturing a luminescence device according to an exemplary embodiment is disposed.

The display device DD may include quantum dots layers EML1, EML2, and EML3, as shown in FIG. 5L. In addition, the display device DD may include luminescence devices LD1, LD2, LD3, as shown in FIG. 5L, including the quantum dots layers EML1, EML2, and EML3. In this exemplary embodiment, the quantum dots layers EML1, EML2, and EML3, may be used as an emission layer which emits light or used as a light control layer which converts a wavelength of light to a long wavelength or transmits a wavelength of light.

Figure 2A:
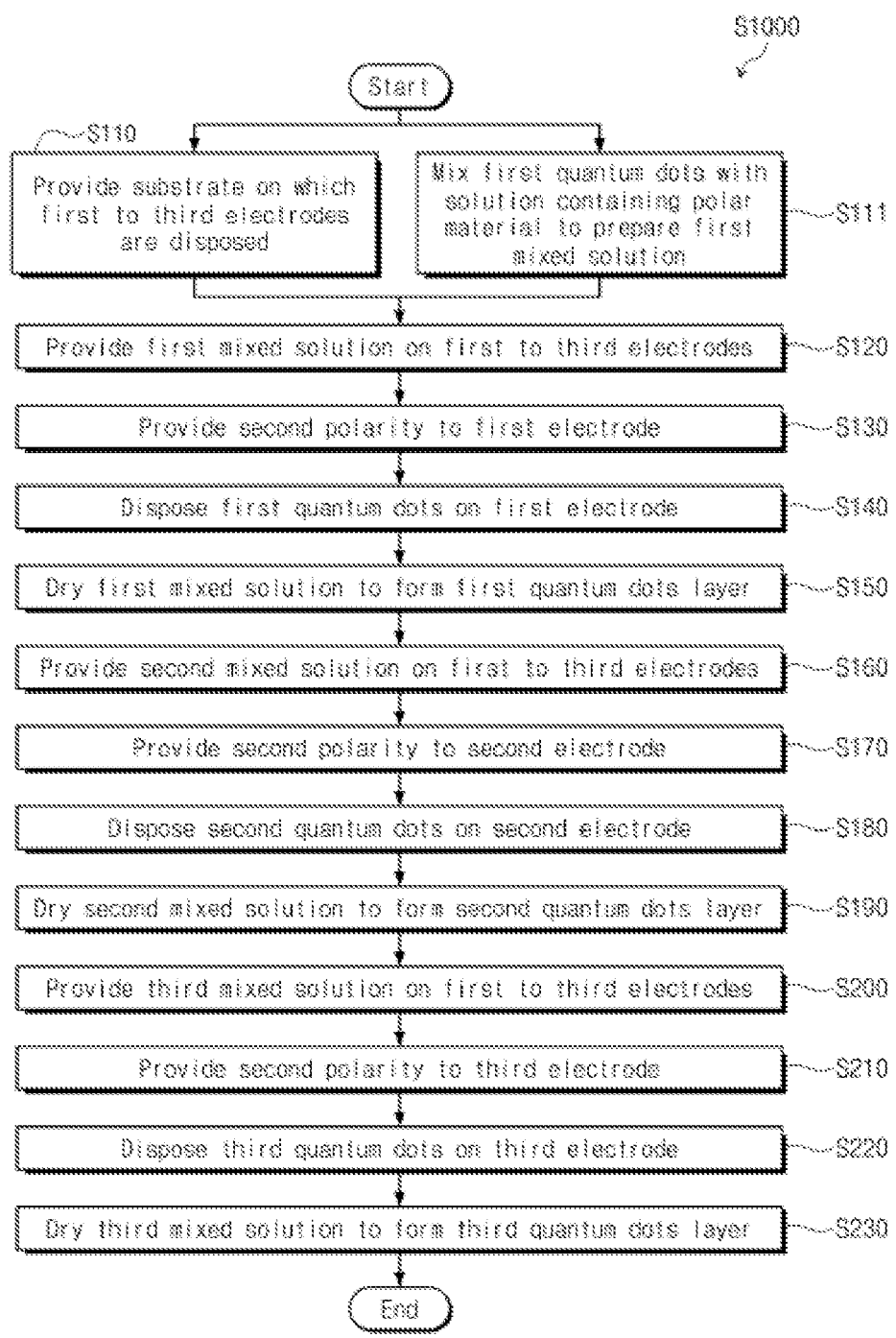
FIG. 2A is a flowchart of a method for manufacturing a quantum dots layer according to an exemplary embodiment.
Figure 2B:
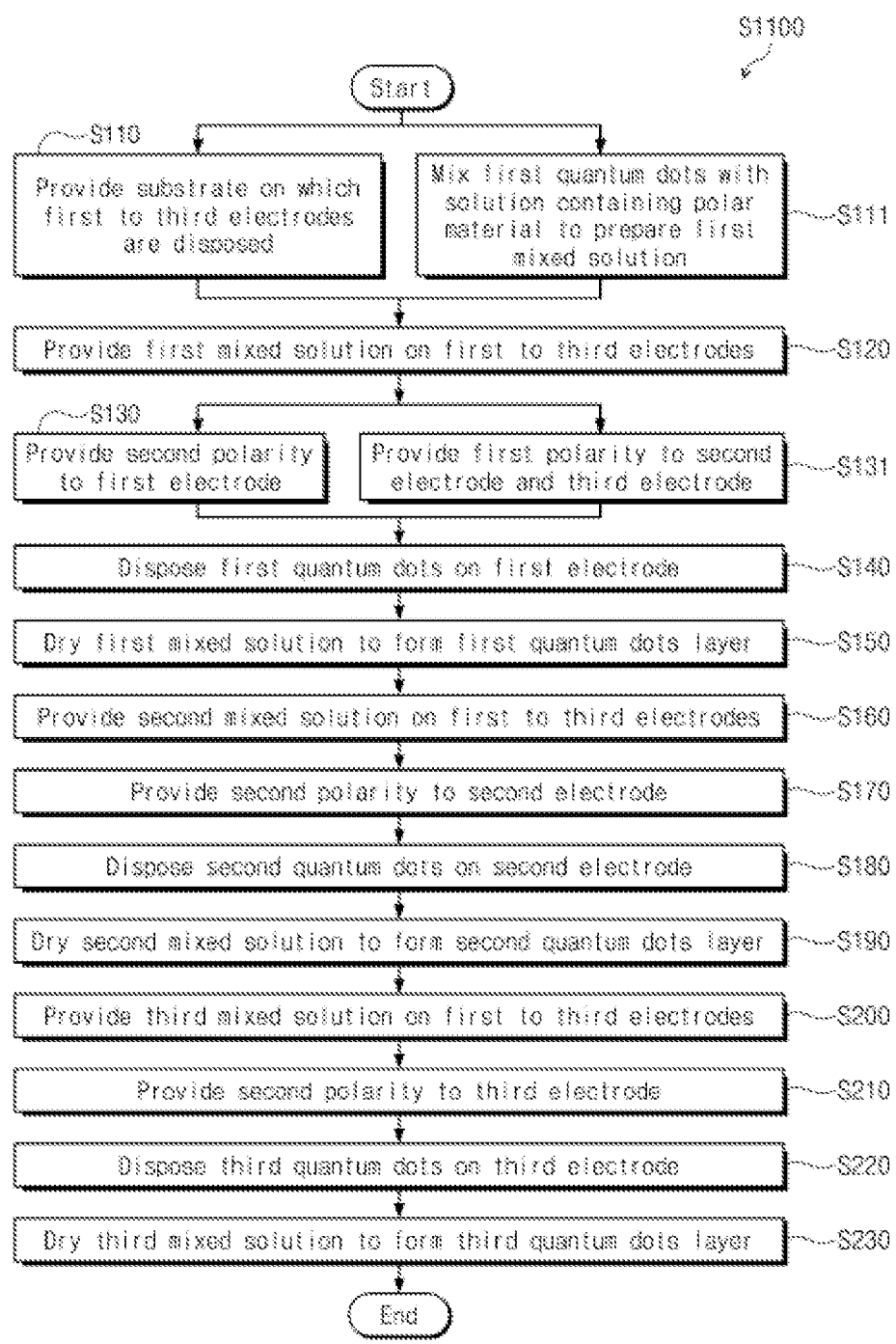
FIG. 2B is a flowchart of a method for manufacturing a quantum dots layer according to an exemplary embodiment.

FIGS. 2A and 2B are flowcharts of methods S1000 and S1100 for manufacturing quantum dots layers EML1, EML2, and EML3, according to an exemplary embodiment. FIGS. 5A to 5K are figures illustrating respective steps of the methods S1000 and S1100 for manufacturing the quantum dots layers EML1, EML2, and EML3 according to an exemplary embodiment.

Referring to FIG. 2A, the method S1000 for manufacturing quantum dots layers EML1, EML2, and EML3 may include: a step S110 for providing a substrate SUB on which first to third electrodes EL1-1, EL1-2, and EL1-3 are formed; a step S111 for preparing a first mixed solution SOL1 by mixing a first quantum dots QD1 with a solution containing a polar material PM, a step S120 for providing the first mixed solution SOL1 on the first to third electrodes EL1-1, EL1-2, and EL1-3; a step S130 for providing a second polarity to the first electrode EL1-1; a step S140 for disposing the first quantum dots QD1 on the first electrode EL1-1; a step S150 for drying the first mixed solution SOL1 to form a first quantum dots layer EML1; a step S160 for providing a second mixed solution SOL2 on the first to third electrodes EL1-1, EL1-2, and EL1-3; a step S170 for providing a second polarity to the second electrode EL1-2; a step S180 for disposing a second quantum dots QD2 on the second electrode EL1-2; a step S190 for drying the second mixed solution SOL2 to form a second quantum dots layer EML2; a step S200 for providing a third mixed solution (not illustrated) on the first to third electrodes EL1-1, EL1-2, and EL1-3; a step S210 for providing a second polarity to the third electrode EL1-3; a step S220 for disposing a third quantum dots (not illustrated) on the third electrode EL1-3; and a step S230 for drying the third mixed solution to form a third quantum dots layer EML3.

Referring to FIG. 2B, the method S1100 for manufacturing quantum dots layers EML1, EML2, and EML3 according to an exemplary embodiment may further include a step S131 for providing a first polarity to the second electrode EL1-2 and the third electrode EL1-3.

Figure 3:
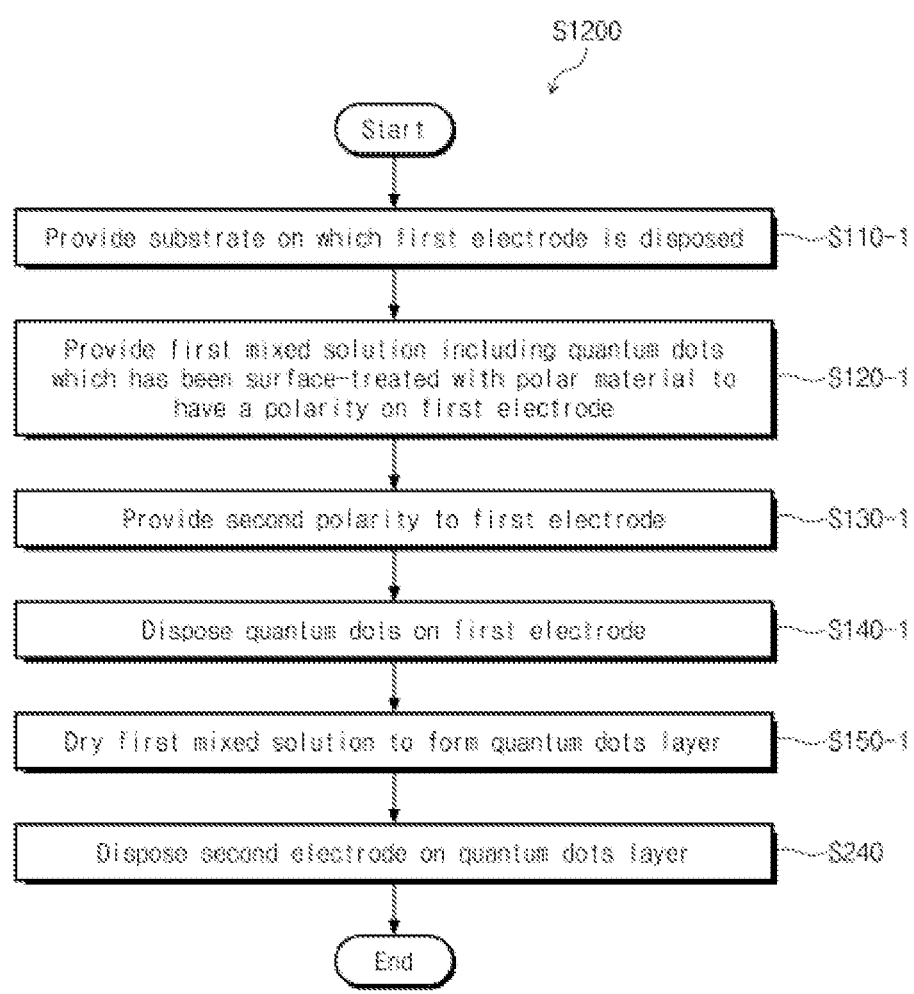
FIG. 3 is a flowchart of a method for manufacturing a luminescence device including a quantum dots layer according to an exemplary embodiment.

FIG. 3 is a flowchart of a method S1200 for manufacturing a luminescence device LD1 including a quantum dots layer EML1 according to an exemplary embodiment.

A detailed description for the manufacturing methods S1000, S1100, and S1200 according to FIGS. 2A, 2B, and 3 will be described later.

Figure 4:
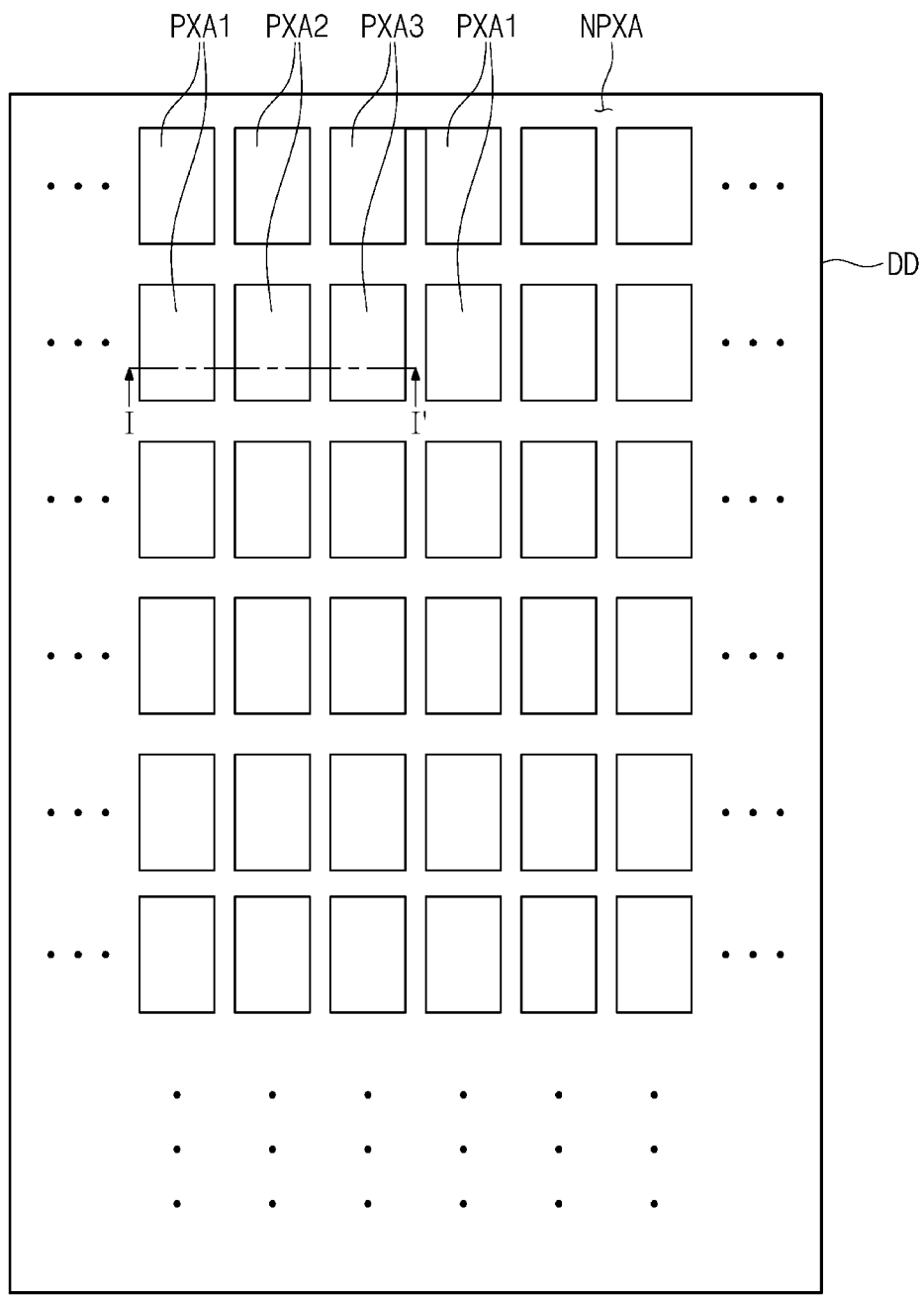
FIG. 4 is a plan view of a display device according to an exemplary embodiment.

FIG. 4 is a plan view of a display device DD according to an exemplary embodiment. FIG. 4 illustrates the display device DD when viewed from above.

Referring to FIG. 4, in the display device DD, first pixel areas PXA1, second pixel areas PXA2, third pixel areas PXA3, and a non-pixel area NPXA may be defined.

The first pixel areas PXA1 may be disposed along the first direction DR1, the second pixel areas PXA2 may be disposed along the first direction DR1, and the third pixel areas PXA3 may be disposed along the first direction DR1. The first pixel areas PXA1, the second pixel areas PXA2, and the third pixel areas PXA3 may be alternately disposed along the second direction DR2. For example, one first pixel area PXA1, one second pixel area PXA2, and one third pixel area PXA3 may be sequentially disposed along the second direction DR2.

The non-pixel area NPXA may be an area disposed adjacent to the first pixel areas PXA1, the second pixel areas PXA2, and the third pixel areas PXA3. The non-pixel region NPXA may set boundaries of the first pixel areas PXA1, the second pixel areas PXA2, and the third pixel areas PXA3.

The first to third pixel areas PXA1, PXA2, and PXA3 may include quantum dots layers EML1, EML2, and EML3 as a luminescence layer or a light control layer.

The first pixel areas PXA1 may provide a first color light, the second pixel areas PXA2 may provide a second color light, and the third pixel areas PXA3 may provide a third color light. The first color light, the second color light, and the third color light may be light having different colors each other. For example, among the first to third color light, one may be blue light, another one may be red light, and the other one may be green light.

Hereinafter, the method S1000 for manufacturing quantum dots layers EML1, EML2, and EML3 of an exemplary embodiment will be described with reference to FIGS. 2A and 5A to 5K. FIGS. 5A to 5K may illustrate areas corresponding to cross-sections taken along a line I-I' in FIG. 4.

FIG. 5A is a cross-sectional view illustrating a step S110 for providing a substrate SUB on which the first to third electrodes EL1-1, EL1-2, and EL1-3 in FIG. 2A are disposed. Referring to FIGS. 2A and 5A, the substrate SUB may include a base substrate BS and a circuit layer CL disposed on the base substrate BS. The circuit layer CL may include a plurality of transistors connected to the first to third electrodes EL1-1, EL1-2, and EL1-3, respectively. The base substrate BS may be a silicon substrate, a plastic substrate, a glass substrate, an insulating film, or a laminated structure including a plurality of insulating layers.

The first to third electrodes EL1-1, EL1-2, and EL1-3, which are spaced apart from each other on a plane, may be disposed on the substrate SUB. A pixel defining layer PDL between the first to third electrodes EL1-1, EL1-2, and EL1-3 may be disposed. In the specification, 'on a plane' may mean that the display device DD is viewed in the third direction (DR3, thickness direction).

The pixel defining layer PDL may overlap a portion of the first to third electrodes EL1-1, EL1-2, and EL1-3 on a plane. Although not illustrated, the pixel defining layer PDL may be omitted.

FIG. 5B is a view illustrating a step S100 for preparing the first mixed solution SOL1 in FIG. 2A.

Referring to FIGS. 5B and 2, a step S111 for preparing a first mixed solution SOL1 by mixing a first quantum dots QD1 with a solution which contains a polar material PM. The number of the first quantum dots QD1 per unit volume in the first mixed solution SOL1 may be adjusted depending on area and thickness of the first quantum dots layer EML1 to be formed.

When the first quantum dots QD1 is mixed with a solution containing the polar material PM, the first quantum dots QD1 may be surface-treated due to the polar material PM to exhibit a polarity.

For example, the polar material PM may react with and bond onto the surface of the first quantum dots QD1 to modify the surface of the first quantum dots QD1, and the surface of the first quantum dots QD1 may exhibit a polarity due to the polarity of the polar material PM. Alternatively, the polar material PM may surround the surface of the first quantum dots QD1 to form a structure similar to a micelle structure, and accordingly, the surface of the first quantum dots QD1 may exhibit a polarity. The polar material PM may be an organic compound. However, the inventive concepts are not limited thereto, and the polar material PM may be a metal compound or an inorganic compound.

Although not illustrated, the first mixed solution SOL1 may contain an acid or a base. The acid or base may be a Bronsted-Lowry acid or a Bronsted-Lowry base, respectively.

FIG. 5C is a perspective view illustrating a quantum dot QD which has been surface-treated with a polar material PM according to an exemplary embodiment. Referring to FIG. 5C, the quantum dot QD which has been surface-treated with the polar material PM may include a base quantum dot QD-B and a polar material which surrounds the base quantum dot QD-B.

The base quantum dot QD-B may be a light-converting particle which absorbs incident light and emits light having a longer wavelength than the incident light. Alternatively, the base quantum dot QD-B may be a self-luminescence particle which is used as a self-luminescence material.

The base quantum dot QD-B, which has a crystal structure of several nanometers in size and is formed of hundreds to thousands of atoms, exhibits a quantum confinement effect in which an energy band gap is increased due to the small size thereof. When the base quantum dot QD-B is irradiated with light having a wavelength higher than the band gap energy, the base quantum dot QD-B is excited by absorbing the light and emits light having a specific wavelength to fall to a ground state. The light having the emitted wavelength has a value corresponding to the band gap. Luminescence characteristics caused by the quantum confinement effect of the base quantum dot QD-B may be adjusted by adjusting size and composition thereof.

The base quantum dot QD-B may be selected from among a Group II-VI compound, a Group III-V compound, a Group IV-VI compound, a Group IV element, a Group IV compound, and a combination thereof.

The Group II-VI compound may be selected from the group consisting of a binary element compound selected from the group consisting of CdSe, CdTe, ZnS, ZnSe, ZnTe, ZnO, HgS, HgSe, HgTe, MgSe, MgS, and a combination thereof; a ternary element compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a combination thereof; and a quaternary element compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a combination thereof.

The Group III-V compound may be selected from the group consisting of a binary element compound selected from the group consisting of GaN, GaP, GaAs, GaSb, AlN, AlP, AlAs, AlSb, InN, InP, InAs, InSb, and a combination thereof; a ternary element compound selected from the group consisting of GaNP, GaNAs, GaNSb, GaPAs, GaPSb, AlNP, AlNAs, AlNSb, AlPAs, AlPSb, InGaP, InNP, InNAs, InNSb, InPAs, InPSb, GaAlNP, and a combination thereof; and a quaternary element compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a combination thereof. The Group IV-VI compound may be selected from the group consisting of a binary element compound selected from the group consisting of SnS, SnSe, SnTe, PbS, PbSe, PbTe, and a combination thereof; a ternary element compound selected from the group consisting of SnSeS, SnSeTe, SnSTe, PbSeS, PbSeTe, PbSTe, SnPbS, SnPbSe, SnPbTe, and a combination thereof; and a quaternary element compound selected from the group consisting of SnPbSSe, SnPbSeTe, SnPbSTe, and a combination thereof. The Group IV element may be selected from the group consisting of Si, Ge, and a combination thereof. The Group IV compound may be a binary element compound selected from the group consisting of SiC, SiGe, and a combination thereof.

At this time, the binary element compound, the ternary element compound, or the quaternary element compound may be present in a particle at a uniform concentration, or may be present in the same particle in which a concentration distribution is partially divided into different states.

The base quantum dot QD-B may be a core-shell structure, including a core CORE and a shell SHELL, which surrounds the core CORE. The base quantum dot QD-B may also have a core CORE/shell SHELL structure, in which one quantum dot surrounds the other quantum dot. An interface between the core CORE and the shell SHELL may have a concentration gradient, in which a concentration of the elements present in the shell SHELL becomes lowered toward the core.

In some exemplary embodiments, the base quantum dot QD-B may have a core-shell structure including a core which contains the described nanocrystal and a shell which surrounds the core. The shell of the base quantum dot QD-B may serve as a protective layer for maintaining semiconductor characteristics by preventing chemical denaturation of the core and/or as a charging layer for giving electrophoresis characteristics to the base quantum dot QD-B. The shell may be a single layer or multiple layers. An interface between the core and the shell may have a concentration gradient in which a concentration of the elements present in the shell becomes lowered toward the core. The shell of the base quantum dot QD-B may include, for example, a metal or nonmetal oxide, a semiconductor compound, or a combination thereof.

The metal or nonmetal oxide may include, for example, a binary element compound, such as $SiO_2$, $Al_2O_3$, $TiO_2$, $ZnO$, MnO, $Mn_2O_3$, $Mn_3O_4$, CuO, FeO, $Fe_2O_3$, $Fe_3O_4$, CoO, $Co_3O_4$, and NiO; or a ternary element compound such as $MgAl_2O_4$, $CoFe_2O_4$, $NiFe_2O_4$, and $CoMn_2O_4$, but the inventive concepts are not limited thereto.

The base quantum dot QD-B may be a particle having a nanometer-scale size. The base quantum dot QD-B may have a full width of half maximum (FWHM) of an emission wavelength spectrum of about 45 nm or less, preferably about 40 nm or less, more preferably about 30 nm or less, and color purity or color reproducibility may be improved in the described range. In addition, light emitted via the base quantum dots QD-B may be emitted in all directions, thereby improving a viewing angle of light.

Furthermore, a shape of the base quantum dots QD-B is not limited to a specific shape typically used in the art, but more specifically, spherical, pyramidal, multi-arm, or cubic nanoparticles, nanotubes, nanowires, nanofibers, nanoplate particles, etc. may be used.

As illustrated in FIG. 5C, when the base quantum dot QD-B is surface-treated with the polar material PM, the polar material PM may surround the surface of the shell SHELL of the base quantum dot QD-B. The polar material PM may either be directly bonded to the shell SHELL of the base quantum dot QD-B or surround the shell SHELL caused by the attraction force. The base quantum dot QD-B may have a first polarity due to the polar material PM. The first polarity may have a positive or negative polarity.

The polar material PM may have an amino group and a silane group. The polar material PM may be, for example, at least one among 3-aminopropyltriethoxysilane (APTES), 3-aminopropyltrimethoxysilane (APTMS), N-(6-aminohexyl)-3-aminopropyltrimethoxysilane (AHAPS), N-(2-aminoethyl)-3-aminopropylmethyldimethoxysilane (AEAPS), 3-aminopropyldimethylethoxysilane (APMES), and 3-(N,N-dimethyl)-aminopropyltrimethoxysilane (DMAPS).

When the polar material PM has an amino group and a silane group, the silane group may surround the base quantum dot QD-B. The amino group may receive hydrogen from the acid present in the mixed solution to form an ammonium ion, and accordingly, the surface of the polar material PM may exhibit a positive polarity.

The polar material PM may have a thiol group and a carboxylic group. The polar material PM may be, for example, at least one selected from among mercaptoacetic acid derivatives, mercaptopropionic acid derivatives, mercaptobutyric acid derivatives, and mercaptovaleric acid derivatives.

When the polar material PM has a thiol group and a carboxyl group, the thiol group may surround the base quantum dot QD-B. The carboxyl group may provide hydrogen to the base present in the mixed solution to form a carboxyl anion, and accordingly, the surface of the polar material PM may exhibit a negative polarity.

The described polar material PM is merely exemplary, and the material is not particularly limited as long as imparting a polarity to the base quantum dot QD-B.

Furthermore, the mechanism through which the surface of the described base quantum dot QD-B exhibits a polarity is exemplary, and the base quantum dot QD-B may exhibit a polarity through other mechanisms depending on the structure and kind of the polar material PM.

FIG. 5D is a cross-sectional view illustrating a step S160 for providing the first mixed solution SOL1 in FIG. 2A on the first to third electrodes EL1-1, EL1-2, and EL1-3. FIG. 5E is a cross-sectional view illustrating a step S130 for providing a second polarity to the first electrode EL1-1 in FIG. 2A, and a step S140 for providing a first polarity to the second electrode EL1-2 and third electrode EL1-3 in FIG. 3.

Referring to FIGS. 2A, 5D, and 5E, the first mixed solution SOL1 may be provided on the first to third electrodes EL1-1, EL1-2, and EL1-3. Thereafter, the second polarity opposite to the first polarity may be provided to the first electrode EL1-1. A method for providing the second polarity to the first electrode EL1-1 is not particularly limited, and various methods which are easily used by those skilled in the art may be used.

When the second polarity is provided to the first electrode EL1-1, an attraction force may occur between a first quantum dots QD1 which has been surface-treated with a polar material to have a first polarity and the first electrode EL1-1. Accordingly, the first quantum point QD1 may be disposed on the first electrode EL1-1. At this time, since the second electrode EL1-2 and the third electrode EL1-3 do not have a second polarity, the first quantum dots QD1 may not be disposed.

FIG. 5F is a cross-sectional view illustrating a step S150 for drying the first mixed solution SOL1 in FIG. 2A to form a first quantum dots layer EML1. Referring to FIGS. 2A and 5F, the first mixed solution SOL1 may be dried to form the first quantum dots layer EML1. When the first mixed solution SOL1 is dried, the first quantum dots QD1 may be fixed on the first electrode EL1-1 to form the first quantum dots layer EML1.

The time and temperature of drying are not particularly limited, and may be adjusted depending on the volume of the first mixed solution SOL1 and the number of the first quantum dots QD1 per unit volume of the first mixed solution SOL1.

Although not illustrated, before the step S160 for providing the first mixed solution SOL1 on the first to third electrodes EL1-1, EL1-2, and EL1-3, a step for disposing a hole transporting region HTR (FIG. 6) on the electrodes EL1-1, EL1-2, and EL1-3 may be further included. In addition, after the drying step, a step for curing or coating the first quantum dots layer EML1 may be further included.

FIG. 5G is a cross-sectional view illustrating a step S160 for providing the second mixed solution SOL2 in FIG. 2A on the first to third electrodes EL1-1, EL1-2, and EL1-3. FIG. 5H is a cross-sectional view illustrating a step S170 for providing a second polarity to the second electrode EL1-2 in FIG. 2A. FIG. 5I is a cross-sectional view illustrating a step S180 for drying the second mixed solution SOL2 in FIG. 2A to form a second quantum dots layer EML2.

Substantially the same contents as those described in FIGS. 5D to 5F may be applied to the respective steps illustrated in FIGS. 5G to 5I, and accordingly, a detailed description will be omitted.

Referring to FIG. 2A, a method S1000 for manufacturing quantum dots layers EML1, EML2, and EML3 may include: a step S200 for providing a third mixed solution (not illustrated) on the first to third electrodes EL1-1, EL1-2, and EL1-3; a step S210 for providing a second polarity to the third electrode EL1-3; a step S220 for disposing the third quantum dots (not illustrated) on the third electrode EL1-3; and a step S230 for drying the third mixed solution to form a third quantum dots layer EML3.

To the step S200 for providing a third mixed solution (not illustrated) on the first to third electrodes EL1-1, EL1-2, and EL1-3, the step S210 for providing a second polarity to the third electrode EL1-3, the step S220 for disposing the third quantum dots (not illustrated) on the third electrode EL1-3, and the step S230 for drying the third mixed solution to form a third quantum dots layer EML3, substantially the same contents as those described in the steps S120, S130, S140, and S150 illustrated in FIGS. 5E to 5F may be applied, and accordingly, a detailed description will be omitted.

Although not illustrated, after the step S230 for drying the third mixed solution (not illustrated) to form the third quantum dots layer EML3, a step for disposing an electron transporting region ETR (FIG. 6) on the first to third quantum dots layers EML1, EML2, and EML3 may be further included.

Hereinafter, a method S1100 for manufacturing quantum dots layers EML1, EML2, and EML3 according to an exemplary embodiment will be described with reference to FIGS. 2B and 5J.

FIG. 5J is a cross-sectional view illustrating a step for providing a first polarity to the second electrode EL1-2 and the third electrode EL1-3 according to an embodiment.

Referring to FIGS. 2B and 5J, the method S1100 for manufacturing the quantum dots layers EML1, EML2, and EML3 according to an exemplary embodiment may further include a step S131 for providing a first polarity to the second electrode EL1-2 and the third electrode EL1-3. The step S131 for providing a first polarity to the second electrode EL1-2 and the third electrode EL1-3 may be performed together with the step S130 for providing a second polarity to the first electrode EL1-1.

The first quantum dots QD1 of this exemplary embodiment is surface-treated with a polar material PM to have a first polarity. Accordingly, when the first polarity is provided to the second electrode EL1-2 and third electrode EL1-3, a repulsive force may occur between the second electrode EL1-2 and third electrode EL1-3, and the first quantum dots QD1. Accordingly, the first quantum dots QD1 may not be disposed on the second electrode EL1-2 and third electrode EL1-3, but may be disposed only on the first electrode EL1-1. Therefore, the first quantum dots QD1 may be selectively disposed only on the first electrode EL1-1.

Although not illustrated, even when each of the second quantum dots QD2 and the third quantum dots (not illustrated) is formed on the second electrode EL1-2 and the third electrode EL1-3, substantially the same contents as those described above may be applied.

FIG. 5K is a cross-sectional view illustrating a substrate SUB on which quantum dots layers EML1, EML2, and EML3, which are formed by the methods S1000 and S1100 for manufacturing quantum dots layers EML1, EML2, and EML3 according to an exemplary embodiment, are disposed.

Referring to FIG. 5K, first to third pixel areas PXA1, PXA2, and PXA3 and a non-pixel area NPXA may be defined by a pixel defining layer PDL. The pixel defining layer PDL may prevent colors from mixing between the first pixel areas PXA1, the second pixel areas PXA2, and the third pixel areas PXA3.

The first quantum dots layer EML1 may overlap the first pixel area PXA1 on a plane, the second quantum dots layer EML2 may overlap the second pixel area PXA2 on a plane, and the third quantum dots layer EML3 may overlap the third pixel area PXA3 on a plane.

The same contents as those described in FIG. 4 may be applied to the first to third pixel areas PXA1, PXA2, and PXA3.

The substrate SUB on which the quantum dots layers EML1, EML2, and EML3 according to an exemplary embodiment are disposed may be disposed on an opposite substrate (not illustrated) on which a separate light-source is disposed. At this time, the separate light-source is not particularly limited, but may be an organic electroluminescence device emitting blue light.

At this time, the quantum dots layers EML1, EML2, and EML3 may serve as a light control layer which absorbs light having a short wavelength emitted from the separate light-source and emits light having a long wavelength. When blue light is emitted from the separate light-source, for example, the first quantum dots layer EML1 may absorb blue light to emit green light or red light. Alternatively, blue light which has a central wavelength different from the blue light emitted from the separate light-source may be emitted.

Referring to FIG. 5K, although FIG. 5K illustrates such that the quantum dots layers EML1, EML2, and EML3 are all formed, but in an exemplary embodiment, only two among the quantum dots layers may be formed. For example, only the first quantum dots layer EML1 and the second quantum dots layer EML2 may be formed. At this time, the area corresponding to the third quantum dots layer EML3 may be an area which transmits light emitted from the separate light-source.

The substrate SUB on which the quantum dots layers EML1, EML2, and EML3 are disposed may be a transparent substrate having an optical transmittance of 90% or more. Accordingly, when light is emitted to the outside from the quantum dots layers EML1, EML2, and EML3, the amount of the light loss caused by passing through the substrate SUB may be minimized. When necessary, a portion of the substrate SUB may be removed by etching, for example.

The first to third electrodes EL1-1, EL1-2, and EL1-3 which are disposed under the quantum dots layers EML1, EML2, and EML3 may be transmissive electrodes. The first to third electrodes EL1-1, EL1-2, and EL1-3 may include transparent metal oxides such as indium tin oxide (ITO), indium zinc oxide (IZO), zinc oxide (ZnO), and indium tin zinc oxide (ITZO).

Hereinafter, a method S1200 for manufacturing a luminescence device LD1 including a quantum dots layer EML1 will be described with reference to FIGS. 3 and 5L.

FIG. 5L is a cross-sectional view illustrating a display device DD in which luminescence devices LD1, LD2, and LD3 formed by the method S1200 for manufacturing a luminescence device according to an exemplary embodiment are disposed.

Referring to FIG. 3, the method S1200 for manufacturing a first luminescence device LD1 including a quantum dots layer EML1 may include: a step S110-1 for providing a substrate on which a first electrode EL1-1 is disposed; a step S120-1 for providing a first mixed solution SOL1 containing a quantum dot QD1 which has been surface-treated with a polar material PM to have a first polarity on the first electrode EL1-1; a step S130-1 for providing a second polarity to the first electrode EL1-1; a step S140-1 for disposing the quantum dot QD1 on the first electrode EL1-1, a step S150-1 for drying the first mixed solution SOL1 to form a quantum dots layer EML1; and a step S240 for disposing a second electrode EL2 on the quantum dots layer EML1.

The steps S110-1, S120-1, S130-1, S140-1, and S150-1 respectively correspond to the steps S110, S120, S130, S140, and S150 illustrated in FIG. 2, and substantially the same description may be applied.

Although the description of the method for manufacturing a second luminescence device LD2 and a third luminescence device LD3 illustrated in FIG. 5L is omitted in FIG. 3, the same description of the method S1200 for manufacturing a first luminescence device LD1 may be applied. For example, after the first to third quantum dots layers EML1, EML2, and EML3 are all formed, the second electrode EL2 may be disposed on the first to third quantum dots layers EML1, EML2, and EML3 to manufacture the first to third luminescence devices LD1, LD2, and LD3.

Since the method S1200 for manufacturing the luminescence device LD1 including the quantum dots layer EML1 of this exemplary embodiment includes the step S240 for disposing the second electrode EL2 on the quantum dots layer EML1, the quantum dots layer EML1, which serves as an emission layer, may be formed.

Referring to FIG. 5L, the quantum dots layers EML1, EML2, and EML3 in the luminescence devices LD1, LD2, and LD3 may serve as an emission layer in an exemplary embodiment.

As the voltages are applied to the first to third electrodes EL1-1, EL1-2, and EL1-3, and the second electrode EL2, respectively, the holes injected from the first to third electrodes EL1-1, EL1-2, and EL1-3 may be moved to the quantum dots layers EML1, EML2, and EML3, and the electrons injected from the second electrode EL2 may also be moved to the quantum dots layers EML1, EML2, and EML3. The electrons and holes may be recombined in the quantum dots layers EML1, EML2, and EML3 to generate excitons, and the excitons may emit light as the excitons fall back from the excited state to the ground state.

At this time, the first quantum dots layer EML1 may emit red light, the second quantum dots layer EML2 may emit green light, and the third quantum dots layer EML3 may emit blue light.

The second electrode EL2 may be a transmissive electrode. The second electrode EL2 may include transparent metal oxides such as indium tin oxide (ITO), indium zinc oxide (IZO), zinc oxide (ZnO), and indium tin zinc oxide (ITZO).

The display device DD in which the luminescence devices LD1, LD2, and LD3 manufactured by the method S1200 for manufacturing luminescence devices LD1, LD2, and LD3, which include the quantum dots layers EML1, EML2, and EML3, are disposed, may emit the quantum dots, which are a luminescence material, by recombining the holes and electrons injected from the first to third electrodes EL1-1, EL1-2, and EL1-3, and the second electrode in the quantum dots layers EML1, EML2, and EML3. At this time, each of the first to third electrodes EL1-1, EL1-2, and EL1-3 may be a transflective electrode or a reflective electrode. The first to third electrodes EL1-1, EL1-2, and EL1-3 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Alternatively, the electrodes may have a structure which has a plurality of layers including: a reflective layer or a transflective layer formed of any among the described materials; and a transparent conductive layer formed of indium tin oxide (ITO), indium zinc oxide (IZO), zinc oxide (ZnO), indium tin zinc oxide (ITZO), etc.

FIG. 6 is a cross-sectional view illustrating a display device DD in which luminescence devices LD1, LD2, and LD3 formed by the method S1200 for manufacturing luminescence devices LD1, LD2, and LD3 according to an exemplary embodiment are disposed. Referring to FIG. 6, each of the luminescence devices LD1, LD2, and LD3 may further include a hole transporting region HTR and an electron transporting region ETR.

The first luminescence device LD1 may include a first quantum dots layer EML1 and emit red light, the second luminescence device LD2 may include a second quantum dots layer EML2 and emit green light, and the third luminescence device LD3 may include a third quantum dots layer EML3 and emit blue light.

The luminescence devices LD1, LD2, and LD3 may be manufactured by the method S1200 for manufacturing luminescence devices LD1, LD2, and LD3 which include the described quantum dots layers EML1, EML2, and EML3. Accordingly, the quantum dots layers EML1, EML2, and EML3 including the quantum dot QD, which has been surface-treated with a polar material PM, may be included.

The hole transporting region HTR may be disposed between the first to third electrodes EL1-1, EL1-2, and EL1-3 and the quantum dots layers EML1, EML2, and EML3, respectively. The hole transporting region HTR may include a hole transporting material and may have a function of effectively transporting holes injected from the first to third electrodes EL1-1, EL1-2, and EL1-3 to the quantum dots layers EML1, EML2, and EML3.

The electron transporting region ETR may be disposed between the quantum dots layers EML1, EML2, and EML3 and the second electrode EL2, respectively. The electron transporting region ETR may include an electron transporting material and may have a function of efficiently transporting electrons injected from the second electrode EL2 to the quantum dots layers EML1, EML2, and EML3.

In the methods S1000, S1100, and S1200 for manufacturing a quantum dots layer EML1 according to an exemplary embodiment and manufacturing a luminescence device LD1 which includes the quantum dots layer EML1, since the quantum dot QD which has been surface-treated with a polar material PM to have a first polarity is disposed on the electrode EL1-1 which is provided with a second polarity opposite to the first polarity, a quantum dots layer EML1 and a luminescence device LD1 including the quantum dots layer EML1 may be manufactured without a mask. In addition, the display device DD according to an exemplary embodiment may be manufactured without using a mask. Accordingly, the large display device may be easily manufactured, and the process cost may be reduced.

According to a method for manufacturing a quantum dots layer according to an exemplary embodiment and a luminescence device which includes the quantum dots layer, a large display device may be manufactured.

According to a method for manufacturing a quantum dots layer according to an exemplary embodiment and a luminescence device which includes the quantum dots layer, process cost may be reduced.

A display device according to an exemplary embodiment may be manufactured without using a mask.

Although certain exemplary embodiments have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A method for manufacturing a quantum dots layer, the method comprising:

provididing a substrate on which a first electrode, a second electrode, and a third electrode, which are laterally spaced apart from each other on a plane, are disposed;

providing a first mixed solution including first quantum dots, which have been surface-treated to have a first polarity, on the first to third electrodes;

providing a second polarity opposite to the first polarity to the first electrode resulting in deposition of the first quantum dots on the first electrode; and drying the first mixed solution to form a first quantum dots layer.

2. The method of claim 1, wherein the providing of the first mixed solution on the first to third electrodes includes mixing a first base quantum dots with a base solution which contains a polar material to prepare a first mixed solution.

3. The method of claim 1, further comprising:
providing a second mixed solution including second quantum dots, which have been surface-treated to have the first polarity, on the first to third electrodes;
providing the second polarity to the second electrode resulting in deposition of the second quantum dots on the second electrode;
drying the second mixed solution to form a second quantum dots layer;
providing a third mixed solution including third quantum dots which have been surface-treated to have the first polarity, on the first to third electrodes;
providing the second polarity to the third electrode resulting in deposition of the third quantum dots on the third electrode; and
drying the third mixed solution to form a third quantum dots layer.

4. The method of claim 2, wherein the first polarity is a positive polarity.

5. The method of claim 4, wherein the polar material is an organic compound having an amino group and a silane group.

6. The method of claim 5, wherein the polar material is at least one selected from the group consisting of 3-aminopropyltriethoxysilane (APTES), 3-aminopropyltrimethoxysilane (APTMS), N-(6-aminohexyl)-3-aminopropyltrimethoxysilane (AHAPS), N-(2-aminoethyl)-3-aminopropylmethyldimethoxysilane (AEAPS), 3-aminopropyldimethylethoxysilane (APMES), and 3-(N,N-dimethyl)-aminopropyltrimethoxysilane (DMAPS).

7. The method of claim 2, wherein the first polarity is a negative polarity.

8. The method of claim 7, wherein the polar material is an organic compound having a thiol group and a carboxyl group.

9. The method of claim 8, wherein the polar material is at least one selected from the group consisting of mercaptoacetic acid derivatives, mercaptopropionic acid derivatives, mercaptobutyric acid derivatives, and mercaptovaleric acid derivatives.

10. The method of claim 1, wherein the first quantum dots layer absorbs blue light and emits red light or green light.

11. The method of claim 1, wherein the substrate has an optical transmittance of at 90% or more.

12. The method of claim 1, wherein the disposing of the first quantum dots further comprises providing the first polarity to the second luminescence electrode and the third luminescence electrode.

13. The method of claim 3, further comprising disposing a second electrode on the first to third quantum dots layers,
wherein the first quantum dots layer emits red light, the second quantum dots layer emits green light, and the third quantum dots layer emits blue light.

* * * * *